United States Patent
Misono

(10) Patent No.: US 8,366,623 B2
(45) Date of Patent: Feb. 5, 2013

(54) ULTRASONIC OBSERVING APPARATUS, CONTROL METHOD FOR ULTRASONIC OBSERVING APPARATUS, ULTRASONIC OBSERVING SYSTEM AND ULTRASONIC DIAGNOSTIC APPARATUS

(75) Inventor: Kazuhiro Misono, Uenohara (JP)

(73) Assignee: Olympus Medical Systems Corp., Tokyo (JP)

( * ) Notice: Subject to any disclaimer, the term of this patent is extended or adjusted under 35 U.S.C. 154(b) by 1330 days.

(21) Appl. No.: 11/818,030

(22) Filed: Jun. 13, 2007

(65) Prior Publication Data

US 2008/0097208 A1    Apr. 24, 2008

(30) Foreign Application Priority Data

Jun. 14, 2006    (JP) ................. 2006-165215

(51) Int. Cl.
*A61B 8/00*    (2006.01)
(52) U.S. Cl. ...................................... 600/441; 600/444
(58) Field of Classification Search .................. 600/441, 600/444
See application file for complete search history.

(56) References Cited

U.S. PATENT DOCUMENTS

| | | | |
|---|---|---|---|
| 4,630,612 A * | 12/1986 | Uchida et al. ................. | 600/441 |
| 5,295,485 A | 3/1994 | Shinomura et al. | |
| 5,680,865 A * | 10/1997 | Tanaka .......................... | 600/441 |
| 5,893,363 A * | 4/1999 | Little et al. .................... | 600/447 |

FOREIGN PATENT DOCUMENTS

| | | |
|---|---|---|
| JP | 06-047043 | 2/1994 |
| JP | 10-33533 | 2/1998 |
| JP | 10-118070 A | 5/1998 |
| JP | 10-277035 A | 10/1998 |
| JP | 10-290799 | 11/1998 |
| JP | 2001-333906 | 12/2001 |
| JP | 2002-515279 A | 5/2002 |
| JP | 2005-312578 A | 11/2005 |
| JP | 2007-037844 | 2/2007 |

OTHER PUBLICATIONS

Japanese Office Action, mailed on Sep. 6, 2011, in counterpart Japanese Patent Application No. 2006-165215.
Japanese Office Action dated Apr. 24, 2012 issued in counterpart Japanese Patent Application No. 2006-165215.

* cited by examiner

*Primary Examiner* — Jonathan Cwern
(74) *Attorney, Agent, or Firm* — Scully, Scott, Murphy & Presser, P.C.

(57) ABSTRACT

An ultrasonic observing apparatus according to the present invention comprises a machine-side connector receptacle, an electronics-side connector receptacle, a mechanical echo signal detecting unit for detecting an echo signal obtained by receiving waves in a mechanical scanning ultrasonic probe connecting to the machine-side connector receptacle, an electronic echo signal detecting unit for detecting an echo signal obtained by receiving waves in an electronic scanning ultrasonic endoscope connecting to the electronics-side connector receptacle, and a signal processing unit for performing signal processing on the echo signal from the mechanical echo signal detecting unit and the echo signal from the electronic echo signal detecting unit.

6 Claims, 9 Drawing Sheets

ULTRASONIC OBSERVING APPARATUS, CONTROL METHOD FOR ULTRASONIC OBSERVING APPARATUS, ULTRASONIC OBSERVING SYSTEM AND ULTRASONIC DIAGNOSTIC APPARATUS

This application claims benefit of Japanese Application No. 2006-165215 filed in Japan on Jun. 14, 2006, the contents of which are incorporated by this reference.

BACKGROUND OF THE INVENTION

1. Field of the Invention

The present invention relates to an ultrasonic observing apparatus, a control method for the ultrasonic observing apparatus, an ultrasonic observing system and an ultrasonic diagnostic apparatus for performing signal processing on an echo signal obtained by transmitting ultrasonic pulses from an ultrasonic transducer to living body tissue and receiving ultrasonic pulses reflected from the living body tissue to create an ultrasonic tomographic image.

2. Description of the Related Art

An ultrasonic diagnostic apparatus, conventionally, repetitively transmits ultrasonic pulses to living body tissue from an ultrasonic transducer and receives an ultrasonic pulse echo signal reflected from the living body tissue to display information in the living body as an ultrasonic tomographic image being a visible image.

There are two types of ultrasonic diagnostic apparatuses depending on the scanning system: electronic scanning to scan a body cavity by electronically driving an ultrasonic transducer built in an ultrasonic endoscope or an ultrasonic probe used by being inserted into a channel for insertion of a treatment instrument of the endoscope, and mechanical scanning to scan the body cavity by mechanically rotating the transducer.

For example, an electronic scanning ultrasonic diagnostic apparatus described in Japanese Patent Laid-Open No. 6-47043 includes an ultrasonic transducer having a plurality of transducer elements. The apparatus drives the transducer elements of the ultrasonic transducer by electronically switching among the devices so that the apparatus can scan a body cavity to obtain an ultrasonic tomographic image.

On the other hand, a mechanical scanning ultrasonic diagnostic apparatus described in Japanese Patent Laid-Open No. 2001-333906 mechanically rotates an ultrasonic transducer so that the apparatus can scan a body cavity to obtain an ultrasonic tomographic image.

The ultrasonic observing apparatus used in the electronic scanning ultrasonic diagnostic apparatus connects to the electronic scanning ultrasonic endoscope or the electronic scanning ultrasonic probe to electronically drive the connected ultrasonic endoscope or ultrasonic probe. Meanwhile, the ultrasonic observing apparatus used in the mechanical scanning ultrasonic diagnostic apparatus connects to the mechanical scanning ultrasonic endoscope or mechanical scanning ultrasonic probe to mechanically drive the connected ultrasonic endoscope or ultrasonic probe.

The mechanical scanning ultrasonic endoscope or mechanical scanning ultrasonic probe mechanically rotates an ultrasonic transducer by 360 degrees to scan a body cavity, so that the scanning range cannot be changed, a frame rate being fixed and a scanning speed being slow. In addition, since the mechanical scanning ultrasonic endoscope or mechanical scanning ultrasonic probe cannot perform transmission for a plurality of times with an ultrasonic transducer being fixed at the same position, a scan is possible only in a B mode but not in a color flow mode.

Consequently, if a conventional mechanical ultrasonic observing apparatus does not need a scan in a color flow mode, arithmetic amount in the ultrasonic observing apparatus is comparatively small and a frame rate does not decrease by arithmetic time.

On the other hand, the electronic scanning ultrasonic endoscope or electronic scanning ultrasonic probe scans a body cavity by electronically driving a plurality of transducer elements composing the ultrasonic transducer, so that a scanning range can be changed to improve a frame rate compared to the mechanical scanning. In addition, the electronic scanning ultrasonic endoscope or electronic scanning ultrasonic probe can change a scanning method, making a scan possible in various modes such as a color flow mode and a power flow mode in addition to a B mode.

SUMMARY OF THE INVENTION

An ultrasonic observing apparatus according to claim 1 of the present invention is configured to comprise:

a first connecting unit for detachably connecting first ultrasonic sending/receiving unit for sending/receiving an ultrasonic wave into/from a body cavity and performing a scan with mechanical scanning;

second connecting unit for detachably connecting second ultrasonic sending/receiving unit for sending/receiving an ultrasonic wave into/from the body cavity and performing a scan with electronic scanning;

scanning identifying unit for identifying the scanning by the first ultrasonic sending/receiving unit connected to the first connecting unit and the scanning by the second ultrasonic sending/receiving unit connected to the second connecting unit; and signal processing unit for performing signal processing on an echo signal of the ultrasonic wave from the first ultrasonic sending/receiving unit or the second ultrasonic sending/receiving unit based on an identification result identified by the scanning identifying unit.

Other features and benefits of the present invention will be fully apparent from the following description.

BRIEF DESCRIPTION OF THE DRAWINGS

FIG. 1 is a block diagram showing an overall configuration of an ultrasonic diagnostic apparatus according to a first embodiment;

FIG. 2 is a block diagram showing the configuration of a signal processing unit in FIG. 1;

FIG. 3 is a block diagram showing the configuration of a memory controller in FIG. 2;

FIG. 4 is a block diagram showing the configuration of a mode sensing unit in FIG. 2;

FIG. 5 is a timing chart showing timing for signals when a first selector in FIG. 4 adds header information from a CPU to an echo signal from an electronic scanning ultrasonic endoscope;

FIG. 6 is a timing chart showing timing for signals of a memory controller, a frame memory, an arithmetic processor and an arithmetic frame memory for an echo signal (a D mode signal) from the electronic scanning ultrasonic endoscope;

FIG. 7 is a timing chart showing timing for signals of a memory controller, a frame memory, a CPU and a graphic memory for an echo signal (a B mode signal) from the electronic scanning ultrasonic endoscope;

FIG. 8 is a block diagram showing a variation of a signal processing unit in FIG. 2; and FIG. 9 is a block diagram showing the configuration of a memory controller in FIG. 8.

DETAILED DESCRIPTION OF THE PREFERRED EMBODIMENTS

In the following, an embodiment of the present invention will be described with reference to the drawings.
(First Embodiment)

Figure 1:
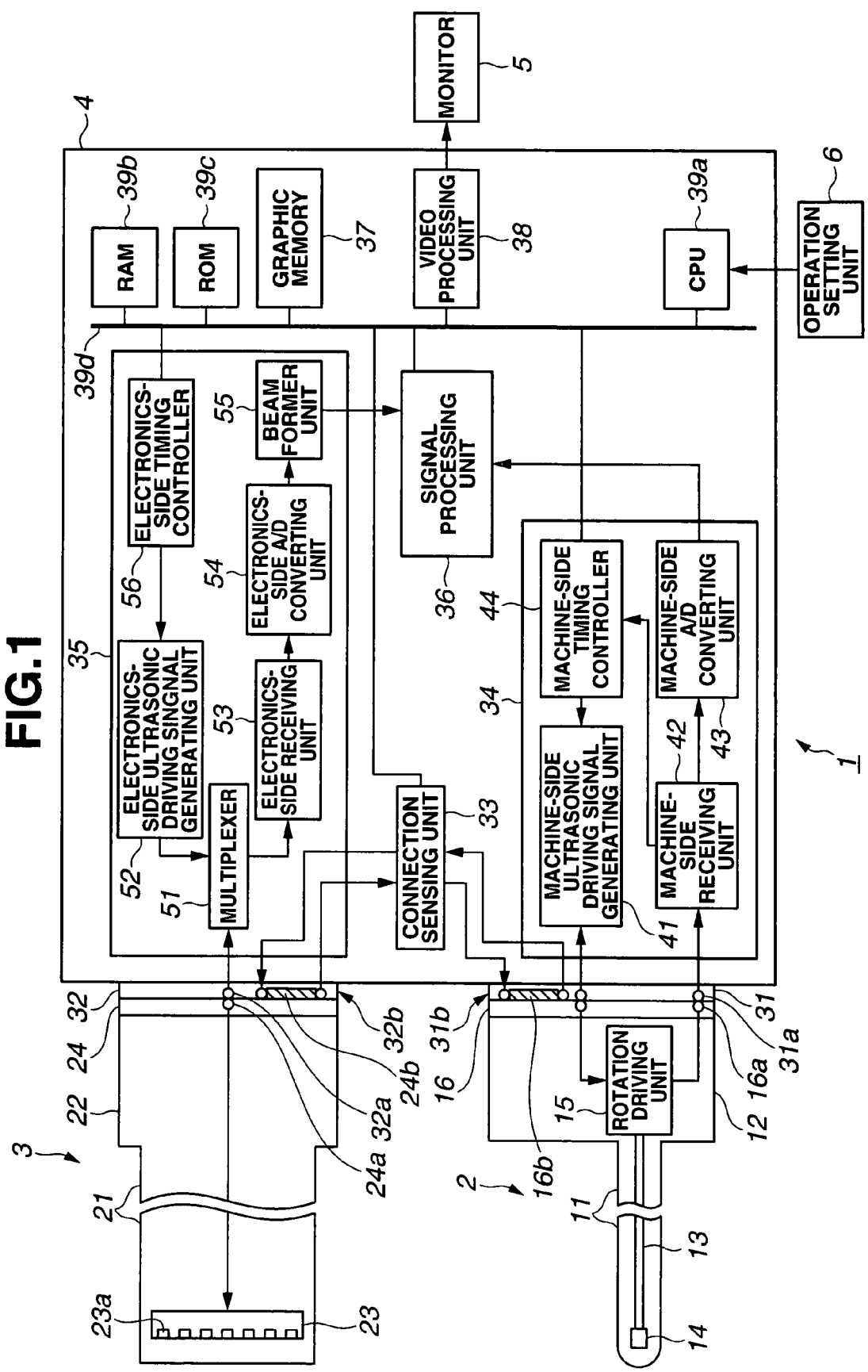
FIGS. 1 to 9 relate to a first embodiment of the present invention.

As shown in FIG. 1, an ultrasonic diagnostic apparatus 1 according to a first embodiment is configured of a mechanical scanning ultrasonic probe 2, an electronic scanning ultrasonic endoscope 3 and an ultrasonic observing apparatus 4. The ultrasonic observing apparatus 4 connects to a monitor 5 and an operation setting unit 6. The present embodiment uses the ultrasonic endoscope for the electronic scanning and the ultrasonic probe for the mechanical scanning.

The electronic scanning uses ultrasonic pulses of about 5 MHz for comparatively deep invasion and image pickup of an observed depth of a subject, enabling detailed diagnosis.

However, if the electronic scanning uses ultrasonic pulses of about 5 MHz, resolution is often insufficient. Therefore, higher frequencies are desired.

In the electronic scanning, a high-resolution ultrasonic probe of 20 to 30 MHz has not been realized because of many technical problems.

On the other hand, in the mechanical scanning, some ultrasonic probes can use ultrasonic pulses of 20 to 30 MHz, making high frequencies usable and enabling improvement of the resolution.

However, since the mechanical scanning does not have a diagnosis mode specific to the electronic scanning such as dynamic focus or color flow, blood flow information, for example, cannot be obtained.

Therefore, if low frequencies and high frequencies of ultrasonic pulses can be used by switching between the frequencies using both of the electronic scanning and the mechanical scanning, and a diagnosis can be made by switching between blood flow information in the electronic scanning and an approachability to an affected part in the machine scanning, various beneficial information can be obtained for an ultrasonic image diagnosis.

According to the present embodiment, the electronic scanning ultrasonic endoscope 3 acquires an entire ultrasonic tomographic image (around a target), and then the mechanical scanning ultrasonic probe 2 acquires a detailed ultrasonic tomographic image.

The ultrasonic observing apparatus 4 can detachably connect to the mechanical scanning ultrasonic probe 2 and the electronic scanning ultrasonic endoscope 3. The ultrasonic observing apparatus 4 obtains echo signals from the connected ultrasonic probe 2 and ultrasonic endoscope 3 to create an ultrasonic tomographic image and displays the ultrasonic tomographic image on the monitor 5.

The mechanical scanning ultrasonic probe 2 includes an insertion portion 11 which is formed long and thin to be inserted easily into a subject and an operation portion 12 provided at a rear end of the insertion portion 11. The mechanical scanning ultrasonic probe 2 is equipped with an ultrasonic transducer 14 on the distal end portion of a flexible shaft 13 inserting through the insertion portion 11.

The rear end portion of the flexible shaft 13 is connected to a rotation driving unit 15 disposed in the operation portion 12.

The rotation driving unit 15 mechanically drives the ultrasonic transducer 14 in a rotational way by rotating the flexible shaft 13 using a motor (not shown). The rotation driving unit 15 is provided with a rotational position detecting unit such as an encoder (not shown). Meanwhile, area around the ultrasonic transducer 14 is filled with ultrasonic propagating media (not shown) for communicating (propagating) ultrasonic waves.

The operation portion 12 is provided with a machine-side connector 16 that detachably connects to the ultrasonic observing apparatus 4. The machine-side connector 16 is provided with a machine-side electric contact unit 16a connecting to a signal line from the rotation driving unit 15. The machine-side connector 16 is also provided with a machine-side connection sensing protrusion unit 16b for sensing that the mechanical scanning ultrasonic probe 2 is connected to the ultrasonic observing apparatus 4.

In the mechanical scanning ultrasonic probe 2, the machine-side connector 16 is connected to the ultrasonic observing apparatus 4, whereby the ultrasonic transducer 14 is electrically connected to the ultrasonic observing apparatus 4 via a signal line inserting through the flexible shaft 13.

The electronic scanning ultrasonic endoscope 3 includes an insertion portion 21 which is formed long and thin to be inserted easily into a subject and an operation portion 22 provided at the rear end portion of the insertion portion 21; at the distal end portion of the insertion portion 21, an ultrasonic transducer 23 is placed. The ultrasonic transducer 23 has a plurality of transducer elements 23a arranged.

The operation portion 22 is provided with an electronics-side connector 24 detachably connected to the ultrasonic observing apparatus 4. The electronics-side connector 24 is provided with an electric contact unit 24a connecting to a signal line from the ultrasonic transducer 23. The electronics-side connector 24 is also provided with an electronics-side connection sensing protrusion unit 24b for sensing that the electronic scanning ultrasonic endoscope 3 is connected to the ultrasonic observing apparatus 4. In the electronic scanning ultrasonic endoscope 3, the electronics-side connector 24 is connected to the ultrasonic observing apparatus 4, whereby the ultrasonic transducer 23 is electrically connected to the ultrasonic observing apparatus 4 via the signal line.

Meanwhile, the electronic scanning ultrasonic endoscope 3 is connected to a light source apparatus and a video processor (not shown). The electronic scanning ultrasonic endoscope 3 is provided with illumination optical system, an objective optical system and an image pickup unit (not shown) at the distal end portion of the insertion portion 21. The electronic scanning ultrasonic endoscope 3 illuminates in a body cavity by the illumination optical system with illumination light supplied from the light source apparatus, and captures light reflected from within the illuminated body cavity as a subject image using the objective optical system to pick up an image with the image pickup unit. The electronic scanning ultrasonic endoscope 3 outputs image pickup signals to a video processor. The video processor performs signal processing on the image pickup signals to generate standard video signals, and outputs the video signals to a monitor for endoscope images to display an endoscope image on the endoscope image monitor.

Additionally, the electronic scanning ultrasonic endoscope 3 includes a treatment instrument inserting channel (not shown). The mechanical scanning ultrasonic probe 2 is inserted through the treatment instrument inserting channel of the electronic scanning ultrasonic endoscope 3 to project from an aperture of the channel such that the probe 2 is inserted into a body cavity.

The ultrasonic observing apparatus 4 includes a machine-side connector receptacle 31 as a first connecting unit detachably connecting to the machine-side connector 16 of the mechanical scanning ultrasonic probe 2, and an electronics-side connector receptacle 32 as a second connecting unit detachably connecting to the electronics-side connector 24 of the electronic scanning ultrasonic endoscope 3.

The machine-side connector receptacle 31 is provided with a receiving-side electric contact unit 31 a contacting and connecting electrically to the machine-side electric contact unit 16a of the machine-side connector 16, and a machine-side fitting unit 31b which a machine-side connection sensing protrusion unit 16b of the machine-side connector 16 fits into. On the other hand, the electronics-side connector receptacle 32 is provided with a receiving-side electric contact unit 32a contacting and connecting electrically to the electric contact unit 24a of the electronics-side connector 24, and an electronics-side fitting unit 32b which the electronics-side connection sensing protrusion unit 24b of the electronics-side connector 24 fits into.

The ultrasonic observing apparatus 4 further includes a connection sensing unit 33, a mechanical transducer echo signal detecting unit (hereinafter, mechanical echo signal detecting unit) 34, an electronic transducer echo signal detecting unit (hereinafter, electronic echo signal detecting unit) 35, a signal processing unit 36, a graphic memory 37, a video processing unit 38, a CPU (central processing unit) 39a, a RAM 39b and a ROM 39c, all of which are electrically connected to each other via a bus 39d.

The connection sensing unit 33 is electrically connected to the machine-side fitting unit 31b and the electronics-side fitting unit 32b, thereby entering a conduction state and senses that the machine-side connector 16 or the electronics-side connector 24 is connected when the machine-side connection sensing protrusion unit 16b or the electronics-side connection sensing protrusion unit 24b is fitted into the machine-side fitting unit 31b or the electronics-side fitting unit 32b. The connection sensing unit 33 outputs a connection sensing signal to the CPU 39a via the bus 39d.

The mechanical echo signal detecting unit 34 transmits ultrasonic pulses toward living body tissue from the ultrasonic transducer 14 that is built in the mechanical scanning ultrasonic probe 2 connected to the machine-side connector receptacle 31, and detects echo signals obtained by receiving ultrasonic pulses reflected from the living body tissue.

The electronic echo signal detecting unit 35 transmits ultrasonic pulses toward living body tissue from the ultrasonic transducer 23 that is built in the electronics scanning ultrasonic endoscope 3 connected to the electronics-side connector receptacle 32, and detects echo signals obtained by receiving ultrasonic pulses reflected from the living body tissue.

The signal processing unit 36 performs signal processing on the echo signals from the mechanical echo signal detecting unit 34 and the electronic echo signal detecting unit 35. The CPU 39a performs polar coordinate transform on the echo signals processed by the signal processing unit 36, then performs image processing and outputs the result to the video processing unit 38.

The video processing unit 38 performs video signal processing and scan transform on display signals processed by the CPU 39a and displays an ultrasonic tomographic image on a display screen of the monitor 5.

The graphic memory 37 temporarily stores the echo signals frame by frame at the video signal processing by the video processing unit 38. The ROM 39c stores a program to control various types of operations of the ultrasonic observing apparatus 4.

The CPU 39a controls the entire ultrasonic observing apparatus 4 based on the program stored in the ROM 39c. As described below, the CPU 39a controls the mechanical echo signal detecting unit 34 and the electronic echo signal detecting unit 35 so as to obtain an ultrasonic tomographic image by controlling either of the mechanical scanning ultrasonic probe 2 or the electronic scanning ultrasonic endoscope 3 based on setting indication inputted from the operation setting unit 6.

The CPU 39a controls a machine-side timing controller 44 or an electronics-side timing controller 56, which will be described below, in a machine mode using the mechanical scanning ultrasonic probe 2 or an electronic mode using the electronic scanning ultrasonic endoscope 3. Further, the CPU 39a outputs scan identification information of the machine mode or the electronic mode to the signal processing unit 36. Furthermore, the CPU 39a controls the electronics-side timing controller 56 to add header information to the echo signals from the electronic scanning ultrasonic endoscope 3, as described below.

Next, the internal configuration of the mechanical echo signal detecting unit 34 will be described in detail.

The mechanical echo signal detecting unit 34 includes a machine-side ultrasonic driving signal generating unit 41, a machine-side receiving unit 42, a machine-side A/D converting unit 43 and the machine-side timing controller 44.

The machine-side ultrasonic driving signal generating unit 41 generates ultrasonic driving pulses based on timing signals from the machine-side timing controller 44 to drive the ultrasonic transducer 14 and outputs the ultrasonic driving pulses. Then, the machine-side ultrasonic driving signal generating unit 41 generates driving signals to drive the rotation driving unit 15 and outputs the driving signals to the rotation driving unit 15.

The machine-side receiving unit 42 receives echo signals from the ultrasonic transducer 14 and processes the signals into analog signals. More particularly, the machine-side receiving unit 42 is configured of an amplifier to amplify echo signals, an LPF (low-pass filter) to prevent aliasing by the machine-side A/D converting unit 43, and a BPF (band-pass filter).

The machine-side A/D converting unit 43 transforms the analog signals processed by the machine-side receiving unit 42 into digital signals and outputs the digital signals to the signal processing unit 36. The machine-side timing controller 44 generates a timing signal based on control by the CPU 39a and a position detecting circuit (not shown) provided with the rotation driving unit 15 and outputs the timing signal to the machine-side ultrasonic driving signal generating unit 41.

Meanwhile, the machine-side timing controller 44 receives a rotational position detection signal from a rotational position detecting unit of the rotation driving unit 15 via the machine-side receiving unit 42, generates a synchronization signal synchronizing with rotation of the ultrasonic transducer 14 and outputs the generated signal to the signal processing unit 36.

Next, internal configuration of the electronic echo signal detecting unit 35 will be described in detail.

The electronic echo signal detecting unit 35 includes a multiplexer 51, an electronics-side ultrasonic driving signal generating unit 52, an electronics-side receiving unit 53, an electronics-side A/D converting unit 54, a beam former unit 55 and the electronics-side timing controller 56.

The multiplexer 51 switches to some of the plurality of transducer elements 23a of the ultrasonic transducer 23 to output ultrasonic driving pulses from the electronics-side ultrasonic driving signal generating unit 52 to a relevant transducer element 23a. Then, the multiplexer 51 outputs echo signals from the relevant transducer element 23a to the electronics-side receiving unit 53.

The electronics-side ultrasonic driving signal generating unit 52 generates a plurality of ultrasonic driving pulses to drive the plurality of transducer elements 23a of the ultrasonic transducer 23 independently based on a timing signal from the electronics-side timing controller 56 and outputs the ultrasonic driving pulses via the multiplexer 51.

The electronics-side receiving unit 53 receives echo signals from the plurality of transducer elements 23a of the ultrasonic transducer 23 via the multiplexer 51 and processes the received echo signals into analog signals. The electronics-side receiving unit 53 is configured of an amplifier, a BPF, a LPF and the like, similar to those of the machine-side receiving unit 42 of the mechanical echo signal detecting unit 34.

The electronics-side A/D converting unit 54 transforms the analog signals processed by the electronics-side receiving unit 53 into digital signals and outputs the digital signals successively. The beam former unit 55 synthesizes echo signals digitized depending on driving of the plurality of transducer elements 23a by delaying the signals based on a timing signal from the electronics-side timing controller 56 and outputs the synthesized signals to the signal processing unit 36.

The electronics-side timing controller 56 generates a timing signal based on control by the CPU 39a and outputs the timing signal to the electronics-side ultrasonic driving signal generating unit 52. The electronics-side timing controller 56 also outputs the generated timing signal to the beam former unit 55. Further, the electronics-side timing controller 56 generates a synchronization signal synchronizing with the echo signal synthesized by the beam former unit 55 and outputs the synchronization signal to a mode sensing unit 62 of the signal processing unit 36 as described below.

As described above, the signal processing unit 36 performs signal processing on the echo signal from the mechanical scanning ultrasonic probe 2 and the electronic scanning ultrasonic endoscope 3 obtained by the mechanical echo signal detecting unit 34 and the electronic echo signal detecting unit 35.

Next, internal configuration of the signal processing unit 36 will be described in detail.

Figure 2:
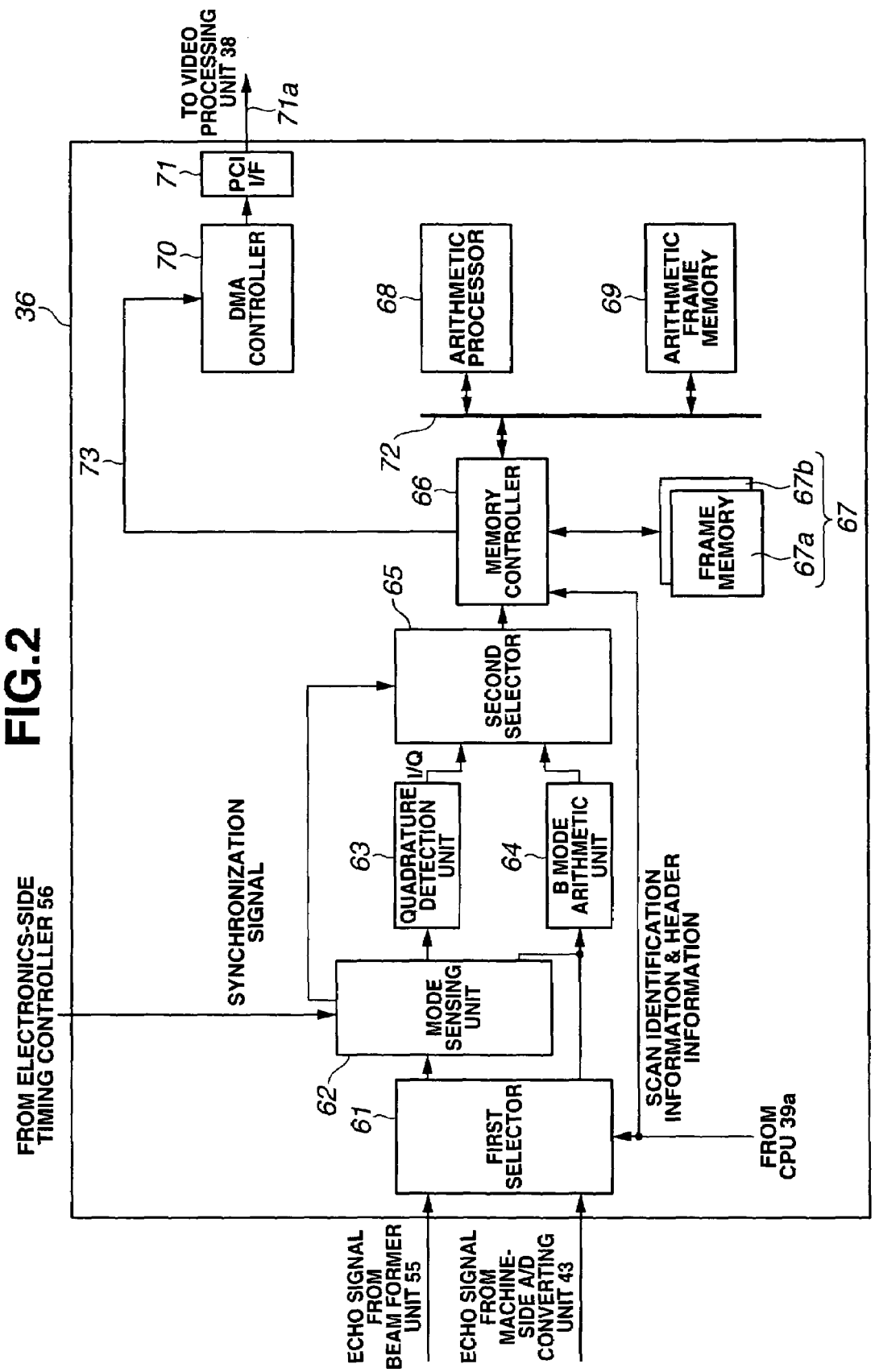

As shown in FIG. 2, the signal processing unit 36 is configured of a first selector 61, the mode sensing unit 62, an quadrature detection unit 63, a B mode arithmetic unit 64, a second selector 65, a memory controller 66, a frame memory 67, an arithmetic processor 68, an arithmetic frame memory 69, a DMA (Direct Memory Access) controller 70 and a PCI interface (I/F) 71.

The memory controller 66, the arithmetic processor 68 and the arithmetic frame memory 69 are connected through a local bus 72. Similarly, the memory controller 66 and the DMA controller 70 are connected through a local bus 73.

The signal processing unit 36 is connected to the video processing unit 38 through the PCI I/F 71 via PCI bus 71a.

The first selector 61 switches between an echo signal from the mechanical scanning ultrasonic probe 2 and an echo signal from the electronic scanning ultrasonic endoscope 3 based on scan identification information from the CPU 39a. Further, the first selector 61 adds header information from the CPU 39a to the echo signal from the electronic scanning ultrasonic endoscope 3.

The mode sensing unit 62 senses whether each frame of an echo signal from the electronic scanning ultrasonic endoscope 3 outputted from the first selector 61 in synchronization with a synchronization signal from the electronics-side timing controller 56 is in a B mode or a D mode based on the added header information and outputs a mode detection signal. Meanwhile, the electronics-side timing controller 56 generates a synchronization signal synchronizing with the echo signal from the electronic scanning ultrasonic endoscope 3 and adds header information to the echo signal according to control by the CPU 39a. A B mode is an image display mode in which echo strength is transformed into brightness enhancement, while a D mode is an image display mode to measure the blood flow rate in a body by applying the Doppler effect and to visualize distribution of the blood flow rate and the intensity of the blood flow.

The mode sensing unit 62 outputs the mode detection signal to the second selector 65. Based on the mode detection signal, the unit 62 outputs an echo signal in a B mode to the B mode arithmetic unit 64 or outputs an echo signal in a D mode to the quadrature detection unit 63. Details of internal configuration of the mode sensing unit 62 will be described below.

The B mode arithmetic unit 64 performs well known arithmetic processing such as filter processing, logarithmic compression processing, envelope detection processing, GAIN processing, contrast processing or sampling processing on an inputted signal, generates a signal representing the echo strength at each reflection point on a sound ray, and generates a B mode signal with an amplitude of the signal at an instance as a luminance value.

The quadrature detection unit 63 performs well known orthogonal detection processing, for example, separates an inputted signal in two, one of which multiplies a sin wave by the inputted signal and the other multiplies a cos wave by the same signal. Confirmation of relative phases of the both signals clarifies a phase of the input signal. The quadrature detection unit 63 outputs the signal as a complex signal I/Q. The arithmetic processor 68 performs autocorrelation on the signal outputted from the quadrature detection unit 63, thereby generating a Doppler signal.

The second selector 65 switches between a D mode signal from the quadrature detection unit 63 and a B mode signal from the B mode arithmetic unit 64 to the memory controller 66 based on a mode detection signal from the mode sensing unit 62. That is, the second selector 65 indicates the destination of a signal to the memory controller 66.

When the mechanical scanning ultrasonic probe 2 inputs a B mode signal, the memory controller 66 stores the B mode signal in the frame memory 67 frame by frame, and outputs a frame of stored signals to the DMA controller 70 via the local bus 73.

Additionally, when the electronic scanning ultrasonic endoscope 3 inputs a B mode signal or a D mode signal, the memory controller 66 stores the signal in the frame memory 67 frame by frame, and outputs a frame of stored signals to the arithmetic processor 68.

Figure 3:
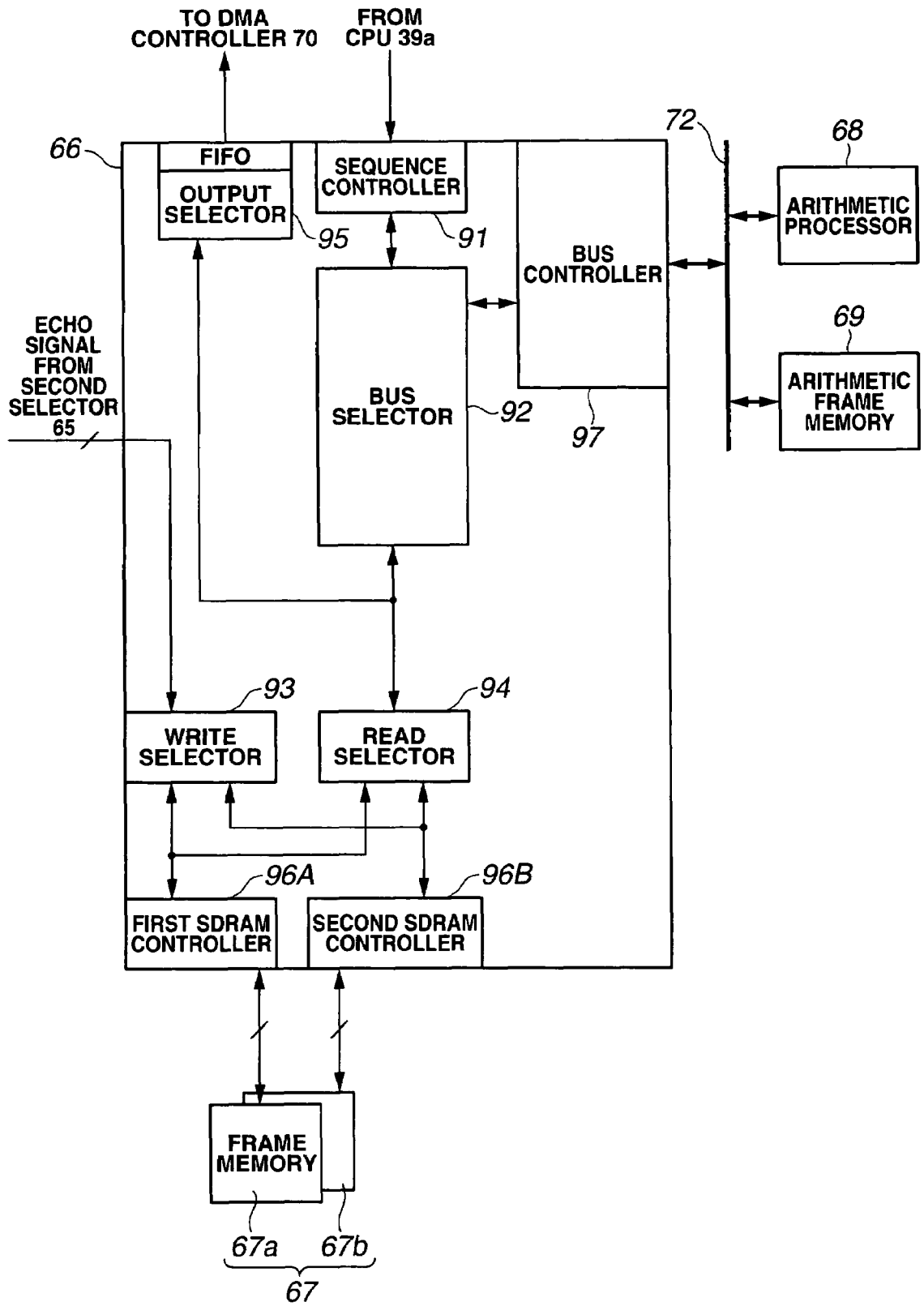

Next, internal configuration of the memory controller 66 will be described in detail with reference to FIG. 3.

The memory controller 66 is configured of a sequence controller 91, a bus selector 92, a write selector 93, a read selector 94, an output selector 95, a first SDRAM controller 96A, a second SDRAM controller 96B and a bus controller 97.

The sequence controller 91 determines mechanical scanning, electronic scanning, a B mode, a color flow mode or the like based on scan identification information from the CPU 39a and header information added to an echo signal. The bus selector 92 changes a route of data according to control by the sequence controller 91. The bus controller 97 is connected to the arithmetic processor 68 via the local bus 72.

The write selector 93 writes an echo signal inputted from the second selector 65 into either of a memory 67a or 67b in the frame memory 67. The read selector 94 reads out an echo signal written in either of the memory 67a or 67b in the frame memory 67. The frame memory 67 is configured of an SDRAM (Synchronous Dynamic Random Access Memory).

Returning to FIG. 2, the frame memory 67 includes the memories 67a and 67b. When data of a first frame is stored in the memory 67a, for example, data of a second frame is stored in the memory 67b and the data of the first frame is read out from the memory 67a to be used alternately.

The arithmetic processor 68 extracts moving components, i.e. blood flow components in tissue using Doppler effect by performing well known processing such as MTI (Moving Target Indicator) filter processing or autocorrelation processing on a D mode signal from the electronic scanning ultrasonic endoscope 3 and creates speed data and power data to color a position of blood flow in an ultrasonic tomographic image for output.

Describing more particularly, the arithmetic processor 68 performs MTI filter processing on the D mode signal from the electronic scanning ultrasonic endoscope 3 so as to obtain Doppler signals (D mode signals) by extracting high-frequency components (blood flow components) only. Further, the arithmetic processor 68 performs autocorrelation on the Doppler signals containing only the blood flow components and calculates a power reflecting the blood flow rate and mainly the blood flow volume based on a deviation frequency at each sample point to form color flow data and power flow data of an image of blood flow. At this time, the arithmetic processor 68 performs threshold processing not to display unnecessary signals other than blood flow on the image of blood flow.

Furthermore, the arithmetic processor 68 does not process a B mode signal from the electronic scanning ultrasonic endoscope 3 and outputs the signal as it is. That is, the arithmetic processor 68 does not perform arithmetic processing on the B mode signal from the electronic scanning ultrasonic endoscope 3, thereby causing the B mode signal to be delayed and behind a D mode signal when the electronic scanning ultrasonic endoscope 3 is used.

For example, the amounts of data in a B mode and a D mode per a frame is as follows:
B mode: 192 lines×512 samples×1×8 bits
D mode: 192 lines×512 samples×16 packets×2×32 bits.

Next, signal flow of mechanical scanning and electronic scanning in the memory controller 66 in a B mode will be described.

For example, if information of a B mode scan for mechanical scanning is inputted from the CPU 39a to the sequence controller 91, the write selector 93 writes a B mode signal inputted from the second selector 65 via the first SDRAM controller 96A into the memory 67a in the frame memory 67. If a frame of data is written into the memory 67a in the frame memory 67, the read selector 94 reads out frame data accumulated in the memory 67a in the frame memory 67 via the first SDRAM controller 96A.

The output selector 95 accumulates the frame data read out from the read selector 94 in an internal FIFO (First In First Out) memory and outputs the data successively to the DMA controller 70 via the local bus 73. As soon as reading out from the memory 67a in the frame memory 67 starts, the write selector 93 writes a next frame of data into the memory 67b in the frame memory 67 via the second SDRAM controller 96B.

By repeating the above operations, the signal processing unit 36 can output an echo signal (a B mode signal) from the mechanical scanning ultrasonic probe 2 to the DMA controller 70 directly, not via the arithmetic processor 68, to increase the signal processing speed. The above operations are similar in B mode processing for the electronic scanning.

Next, signal flow in a diagnosis mode such as a color flow mode specific to electronic scanning in the memory controller 66 will be described.

For example, if information of a scan in a diagnosis mode such as a color flow mode for electronic scanning specific to electronic scanning is inputted from the CPU 39a to the sequence controller 91, the write selector 93 writes a B mode signal inputted from the second selector 65 via the first SDRAM controller 96A into the memory 67a in the frame memory 67.

If a frame of B mode signal is written into the memory 67a in the frame memory 67, the read selector 94 reads out frame data (a B mode signal) accumulated in the memory 67a in the frame memory 67 via the first SDRAM controller 96A. The bus selector 92 transfers the frame data (a B mode signal) read out from the read selector 94 depending on control by the sequence controller 91 into the arithmetic frame memory 69 via the bus controller 97.

When the data transfer of the frame data (a B mode signal) to the arithmetic frame memory 69 is complete, the write selector 93 writes a D mode signal inputted from the second selector 65 via the second SDRAM controller 96B into the memory 67b in the frame memory 67. The arithmetic processor 68 performs arithmetic processing on frame data in the arithmetic frame memory 69 while the ultrasonic endoscope 3 performs D mode scanning. However, since the frame data in the arithmetic frame memory 69 is a B mode signal, the frame data is outputted without being processed.

The bus selector 92 reads out the frame data (a B mode signal) accumulated in the arithmetic frame memory 69 and outputs the frame data to the DMA controller 70 via the bus controller 97 and the FIFO memory in the output selector 95.

If a frame of D mode signal is written into the memory 67b in the frame memory 67, the read selector 94 reads out frame data (a D mode signal) accumulated in the memory 67b in the frame memory 67 via the second SDRAM controller 96B. The bus selector 92 transfers the frame data (a D mode signal) read out from the read selector 94 depending on control by the sequence controller 91 into the arithmetic frame memory 69 via the bus controller 97.

When the data transfer of the frame data (a D mode signal) to the arithmetic frame memory 69 is complete, the write selector 93 writes a B mode signal inputted from the second selector 65 via the first SDRAM controller 96A into the memory 67a in the frame memory 67. The arithmetic processor 68 performs arithmetic processing on a D mode signal in the arithmetic frame memory 69 while the ultrasonic endoscope 3 performs B mode scanning.

The bus selector 92 reads out the frame data (a D mode signal) accumulated in the arithmetic frame memory 69 and outputs the frame data to the DMA controller 70 via the bus controller 97 and the FIFO memory in the output selector 95.

By repeating the above operations, the signal processing unit 36 performs signal processing on an echo signal (a D mode signal) from the electronic scanning ultrasonic endoscope 3 using the arithmetic processor 68 and outputs the result to the DMA controller 70.

The DMA controller 70 outputs the frame of data to the video processing unit 38 via the PCI I/F 71.

Figure 4:
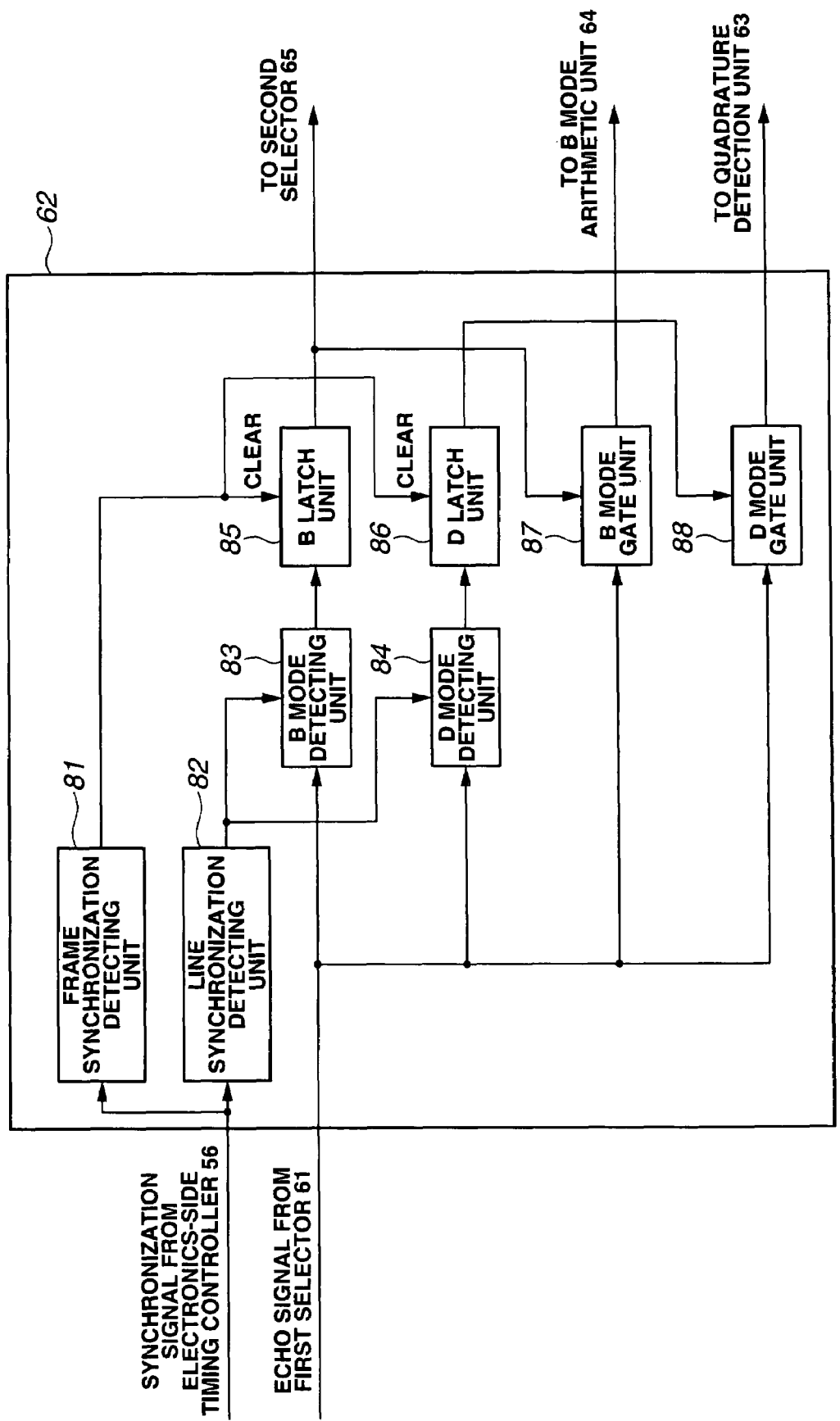

Next, internal configuration of the mode sensing unit 62 will be described in detail with reference to FIG. 4.

The mode sensing unit 62 is configured of a frame synchronization detecting unit 81, a line synchronization detecting unit 82, a B mode detecting unit 83, a D mode detecting unit 84, a B latch unit 85, a D latch unit 86, a B mode gate unit 87 and a D mode gate unit 88.

The frame synchronization detecting unit 81 detects a frame synchronization signal from synchronization signals from the electronics-side timing controller 56 and outputs the detected frame synchronization signal to the first and second latch units 85 and 86. Meanwhile, the line synchronization detecting unit 82 detects a line synchronization signal from synchronization signals from the electronics-side timing controller 56 and outputs the detected line synchronization signal to the B mode detecting unit 83 and the D mode detecting unit 84.

The B mode detecting unit 83 detects that an echo signal (a B mode signal) from the electronic scanning ultrasonic endoscope 3 is in a B mode based on added header information according to a line synchronization signal from the line synchronization detecting unit 82 and outputs the B mode detection signal to the B latch unit 85.

The B latch unit 85 latches a B mode detection signal from the B mode detecting unit 83 till a frame synchronization signal from the frame synchronization detecting unit 81 is inputted. When a frame detection result is inputted, the unit 85 outputs the latched B mode detection signal to the second selector 65 and the B mode gate unit 87 and clears the latched data.

The B mode gate unit 87 passes an echo signal (a B mode signal) through from the electronic scanning ultrasonic endoscope 3 based on a B mode detection signal from the B latch unit 85 and output the signal to the B mode arithmetic unit 64. On the other hand, the D mode detecting unit 84 detects that an echo signal (a D mode signal) from the electronic scanning ultrasonic endoscope 3 is in a D mode based on added header information according to a line synchronization signal from the line synchronization detecting unit 82 and outputs the D mode detection signal to the D latch unit 86.

The D latch unit 86 latches a D mode detection signal from the D mode detecting unit 84 till a frame synchronization signal from the frame synchronization detecting unit 81 is inputted. When a frame detection result is inputted, the unit 86 outputs the latched D mode detection signal to the second selector 65 and the D mode gate unit 88 and clears the latched data.

The D mode gate unit 88 passes an echo signal (a D mode signal) through from the electronic scanning ultrasonic endoscope 3 based on a D mode detection signal from the D latch unit 86 and outputs the signal to the quadrature detection unit 63.

The operation of the ultrasonic diagnostic apparatus 1 configured as described above will be described.

As shown in FIG. 1, the ultrasonic diagnostic apparatus 1 performs ultrasonic observation with the mechanical scanning ultrasonic probe 2 and the electronic scanning ultrasonic endoscope 3 being connected to the ultrasonic observing apparatus 4. The electronic scanning ultrasonic endoscope 3 is also connected to a light source apparatus and a video processor (not shown).

The machine-side connector 16 of the mechanical scanning ultrasonic probe 2 is detachably connected to the machine-side connector receptacle 31 of the ultrasonic observing apparatus 4. The machine-side electric contact unit 16a of the machine-side connector 16 electrically contacts and connects to the receiving-side electric contact unit 31a, while the machine-side connection sensing protrusion unit 16b fits in the machine-side fitting unit 31b. With this configuration, the mechanical scanning ultrasonic probe 2 electrically connects to the mechanical echo signal detecting unit 34 in the ultrasonic observing apparatus 4. The mechanical echo signal detecting unit 34 makes the rotation driving unit 15 and the ultrasonic transducer 14 controllable.

At this time, the connection sensing unit 33 conducts by fitting the machine-side connection sensing protrusion unit 16b in the machine-side fitting unit 31b to sense that the machine-side connector 16 is connected. The connection sensing unit 33 outputs a connection sensing signal to the CPU 39a via the bus 39d. Based on the signal, the CPU 39a in the ultrasonic observing apparatus 4 senses that the mechanical scanning ultrasonic probe 2 is connected.

On the other hand, the electronics-side connector 24 of the electronic scanning ultrasonic endoscope 3 is detachably connected to the electronics-side connector receptacle 32 of the ultrasonic observing apparatus 4. The electronics-side electric contact unit 24a of the electronics-side connector 24 electrically contacts and connects to the receiving-side electric contact unit 32a, while the electronics-side connection sensing protrusion unit 24b fits in the electronics-side fitting unit 32b. With this configuration, the electronic scanning ultrasonic endoscope 3 electrically connects to the electronic echo signal detecting unit 35 in the ultrasonic observing apparatus 4. The electronic echo signal detecting unit 35 makes the ultrasonic transducer 23 controllable.

At this time, the connection sensing unit 33 conducts by fitting the electronics-side connection sensing protrusion unit 24b in the electronics-side fitting unit 32b to sense that the electronics-side connector 24 is connected. The connection sensing unit 33 outputs a connection sensing signal to the CPU 39a via the bus 39d. Based on the signal, the CPU 39a in the ultrasonic observing apparatus 4 senses that the electronic scanning ultrasonic endoscope 3 is connected.

First, an operator inserts the electronic scanning ultrasonic endoscope 3 into a body cavity and guides the distal end portion of an insertion portion to a target. The electronic scanning ultrasonic endoscope 3 illuminates the body cavity from illumination optical system with illumination light supplied from a light source apparatus. The electronic scanning ultrasonic endoscope 3 captures reflected light in the illuminated body cavity as a subject image by the objective optical system to pick up an image with an image pickup unit and outputs an image pickup signal to a video processor. The video processor performs signal processing on the image pickup signal and outputs the obtained video signal to an endoscope image monitor to display an endoscope image on the display screen of the monitor. The operator, while viewing the endoscope image using the endoscope image monitor, reaches the insertion portion distal end portion of the electronic scanning ultrasonic endoscope 3 to the target in the body cavity.

Next, the operator operates the operation setting unit 6 and performs ultrasonic observation around the target using the electronic scanning ultrasonic endoscope 3. The ultrasonic observing apparatus 4 controls the electronic scanning ultrasonic endoscope 3 based on setting indication information inputted by the CPU 39a from the operation setting unit 6. Assume here that the operator has selected a color flow mode.

The CPU 39a receives a connection detecting signal from the connection sensing unit 33, thereby recognizing that the electronic scanning ultrasonic endoscope 3 is connected. The CPU 39a controls the electronics-side timing controller 56 to output the timing signal to the electronics-side ultrasonic driving signal generating unit 52. The electronics-side ultrasonic driving signal generating unit 52 generates ultrasonic driving pulses separately to each of the transducer elements 23*a* of the ultrasonic transducer 23 based on the timing signal from the electronics-side timing controller 56, and outputs the generated ultrasonic driving pulses to relevant transducer elements 23*a* via the multiplexer 51.

Each of the transducer elements 23*a* of the ultrasonic transducer 23 generates ultrasonic pulses, whereby the electronic scanning ultrasonic endoscope 3 receives the ultrasonic pulses from the living body tissue to successively obtain echo signals. The echo signals are separately received via the multiplexer 51 and successively subjected to analog signal processing by the electronics-side receiving unit 53.

The processed echo signals are transformed into digital signals by the electronics-side A/D converting unit 54 and synthesized by the beam former unit 55 by being delayed depending on the driving of relevant transducer elements 23*a*. The synthesized signals are outputted to the signal processing unit 36.

At this time, the electronics-side timing controller 56 outputs a synchronization signal to the mode sensing unit 62 of the signal processing unit 36. Meanwhile, the CPU 39*a* outputs header information to the mode sensing unit 62 of the signal processing unit 36 and adds the header information to an echo signal from the electronic scanning ultrasonic endoscope 3.

In the signal processing unit 36, the first selector 61 switches the echo signal from the electronic scanning ultrasonic endoscope 3 based on scan identification information from the CPU 39*a*. Additionally, the first selector 61 adds the header information from the CPU 39*a* to the echo signal from the electronic scanning ultrasonic endoscope 3, as shown in FIG. 5.

Figure 5:
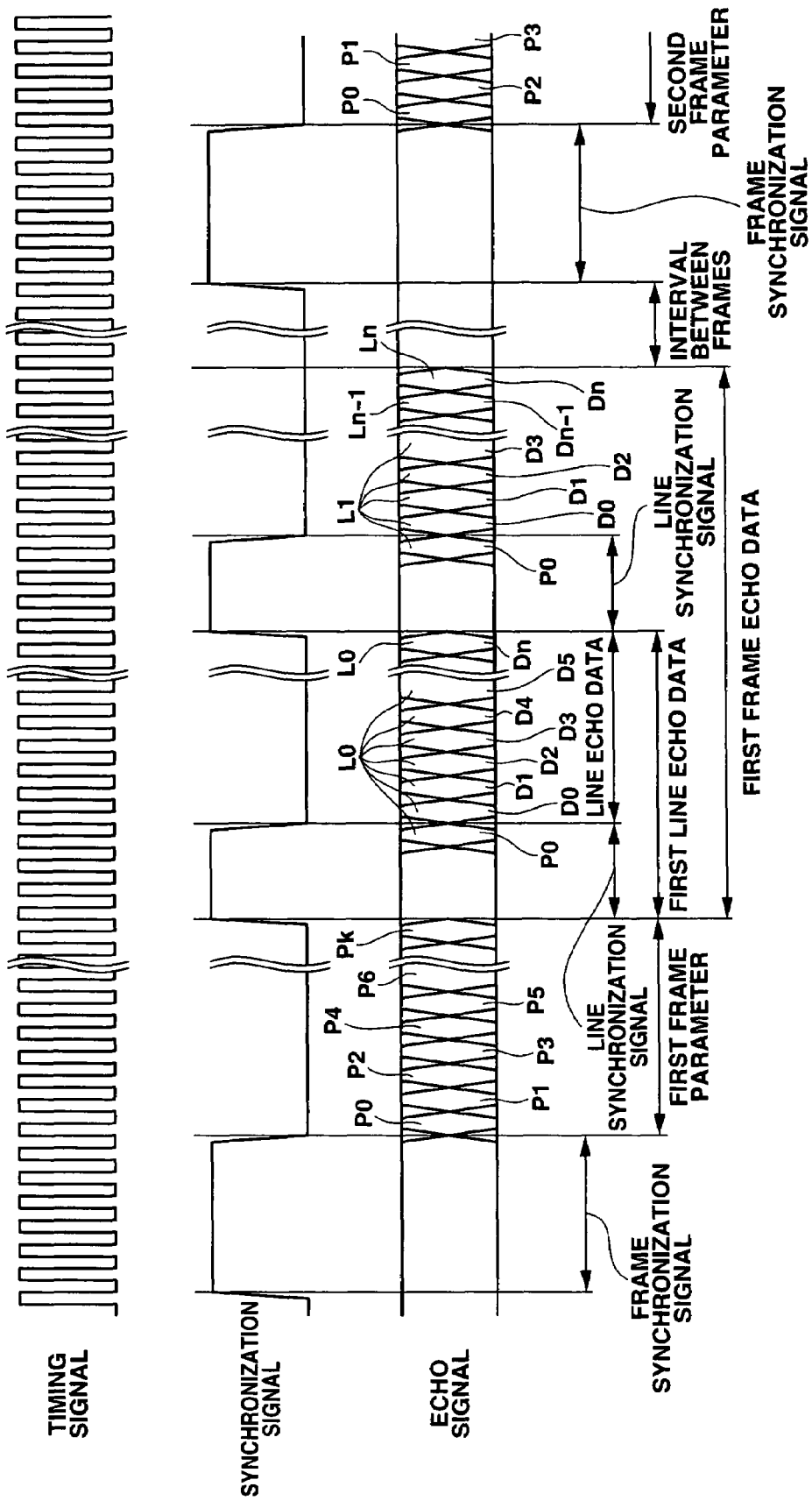

In FIG. 5, the top column represents timing signals, the middle column represents frame synchronization signals and line synchronization signals, and the bottom column represents echo signals. An echo signal is supplemented with a first frame parameter as header information next to a frame synchronization signal, which is followed by first frame echo data; after an interval between frames, the echo signal is again supplemented with a second frame parameter, which is followed by second frame echo data, and the signals are repeated for pre-determined frames.

The first frame echo data is formed of the first to, for example, 512 line echo data, each of which follows a line synchronization signal as the header information. In FIG. 5, P indicates a parameter, L indicates a line No. and D indicates echo data. In FIG. 5, data D is represented as D0 to Dn.

Parameters from the first frame to a pre-determined frame includes, for example, P0 to Pk followed by frame echo data, for which it can be detected whether the frame echo data is in a B mode or a D mode. Meanwhile, the head of line echo data from the first line to the 512 line includes a parameter of header information of relevant line echo data. The parameter is followed by line echo data, for which it can be detected whether the line echo data is in a B mode or a D mode.

For the echo signal from the electronic scanning ultrasonic endoscope 3 supplemented with the header information by the first selector 61 as described above, it is sensed whether the echo signal is in a B mode or a D mode frame by frame in synchronization with a synchronization signal from the electronics-side timing controller 56 by the mode sensing unit 62.

The mode sensing unit 62 detects a B mode according to the header information added line by line by the B mode detecting unit 83 based on the line synchronization signal detected by the line synchronization detecting unit 82, and outputs a B mode detection signal to the B latch unit 85. The mode sensing unit 62 outputs the B mode detection signal from the B latch unit 85 to the second selector 65 and the B mode gate unit 87 frame by frame based on the frame synchronization signal detected by the frame synchronization detecting unit 81. The B mode gate unit 87 outputs an echo signal in a B mode to the B mode arithmetic unit 64 frame by frame based on the B mode detection signal.

On the other hand, the mode sensing unit 62 detects a D mode according to the header information added line by line by the D mode detecting unit 84 based on the line synchronization signal detected by the line synchronization detecting unit 82, and outputs a D mode detection signal to the D latch unit 86. The mode sensing unit 62 outputs the D mode detection signal from the D latch unit 86 to the second selector 65 and the D mode gate unit 88 frame by frame based on the frame synchronization signal detected by the frame synchronization detecting unit 81. The D mode gate unit 88 outputs an echo signal in a D mode to the quadrature detection unit 63 frame by frame based on the D mode detection signal.

Frames of echo signals inputted to the B mode arithmetic unit 64 are each transformed into B mode signals according to well known arithmetic processing and outputted to the memory controller 66 via the second selector 65.

Frames of B mode signals inputted to the memory controller 66 are each temporarily stored in the frame memory 67 as described above, and then outputted to the video processing unit 38 from the DMA controller 70 via the PCI I/F 71.

On the other hand, frames of echo signals inputted to the quadrature detection unit 63 are each transformed into Doppler signals (D mode signals) according to well known orthogonal detection processing, and outputted to the memory controller 66 via the second selector 65.

Frames of D mode signals inputted to the memory controller 66 are each temporarily stored in the frame memory 67 as described above, and then undergo well known processing such as MTI filter processing or autocorrelation processing by the arithmetic processor 68 to be transformed into color flow data (Doppler data) of an image of blood flow. The color flow data is outputted to the video processing unit 38 from the DMA controller 70 via the PCI I/F 71.

Figure 6:
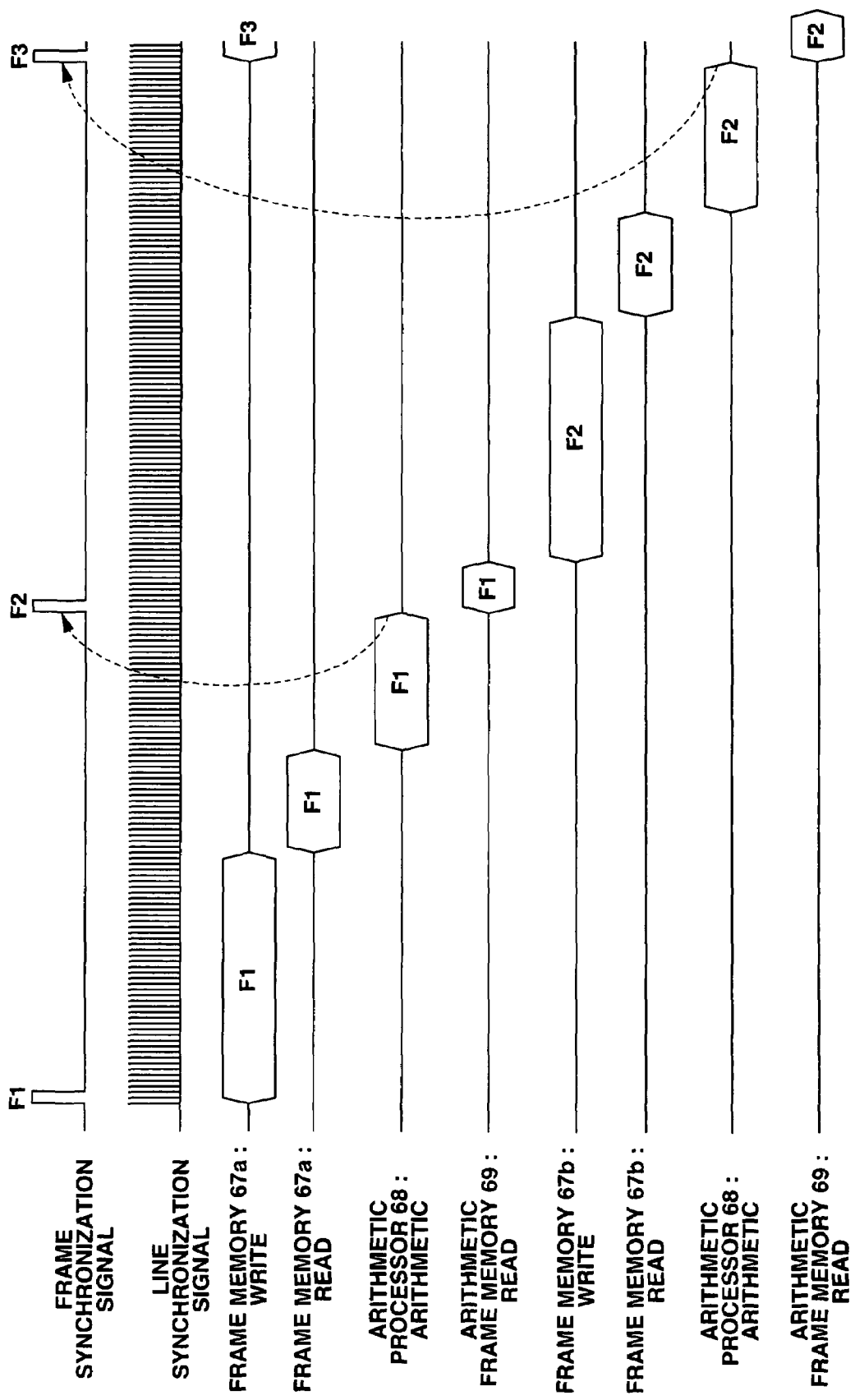

The memory controller 66, the frame memory 67, the arithmetic processor 68 and the arithmetic frame memory 69 operate as shown in FIG. 6, for example.

In FIG. 6, the first column represents frame synchronization signals and the second column represents line synchronization signals. The third column represents write of a D mode signal of a first frame into the memory 67*a* in the frame memory 67. The fourth column represents read of the D mode signal of the first frame from the memory 67*a* in the frame memory 67. The fifth column represents arithmetic on the D mode signal of the first frame by the arithmetic processor 68. The sixth column represents read of the D mode signal of the first frame from the arithmetic frame memory 69.

The seventh column represents write of a D mode signal of a second frame into the memory 67*b* in the frame memory 67. The eighth column represents read of the D mode signal of the second frame from the memory 67*b* in the frame memory 67. The ninth column represents arithmetic on the D mode signal of the second frame by the arithmetic processor 68. The tenth column represents read of the D mode signal of the second frame from the arithmetic frame memory 69.

The D mode signal obtained from the electronic scanning ultrasonic endoscope 3 as described above undergoes arithmetic processing by the arithmetic processor 68 to be transformed into color flow data (Doppler data) of an image of blood flow, and is outputted to the video processing unit 38 from the DMA controller 70 via PCI I/F 71.

The video processing unit 38 performs video signal processing such as coordinate transform using the graphic memory 37 according to control by the CPU 39a and displays a color flow image as an ultrasonic tomographic image on the display screen of the monitor 5 with a background image of a monochrome B mode image.

The operator can observe the state of blood flow in the target by viewing the color flow image displayed on the display screen of the monitor 5. Additionally, the operator performs ultrasonic diagnosis based on a B mode image using the electronic scanning ultrasonic endoscope 3.

The ultrasonic observing apparatus 4 controls the electronic scanning ultrasonic endoscope 3 based on setting indication information inputted to the CPU 39a from the operation setting unit 6. The CPU 39a controls the electronics-side timing controller 56 to output the timing signal to the electronics-side ultrasonic driving signal generating unit 52. The electronics-side ultrasonic driving signal generating unit 52 generates ultrasonic driving pulses separately to each of the transducer elements 23a of the ultrasonic transducer 23 based on the timing signal from the electronics-side timing controller 56, and outputs the generated ultrasonic driving pulses to relevant transducer elements 23a via the multiplexer 51.

Each of the transducer elements 23a of the ultrasonic transducer 23 generates ultrasonic pulses, whereby the electronic scanning ultrasonic endoscope 3 receives the ultrasonic pulses from the living body tissue to successively obtain echo signals. The echo signals are separately received via the multiplexer 51 and successively subjected to analog signal processing by the electronics-side receiving unit 53.

The analog processed echo signals are transformed into digital signals by the electronics-side A/D converting unit 54 and synthesized by the beam former unit 55 by being delayed depending on the driving of relevant transducer elements 23a. The synthesized signals are outputted to the signal processing unit 36.

At this time, the electronics-side timing controller 56 outputs a synchronization signal to the mode sensing unit 62 of the signal processing unit 36. Meanwhile, the CPU 39a outputs header information to the mode sensing unit 62 of the signal processing unit 36 and adds the header information to an echo signal from the electronic scanning ultrasonic endoscope 3.

In the signal processing unit 36, the first selector 61 switches the echo signal from the electronic scanning ultrasonic endoscope 3 based on scan identification information from the CPU 39a. Additionally, the first selector 61 adds the header information from the CPU 39a to the echo signal from the electronic scanning ultrasonic endoscope 3, as described above.

For the echo signal from the electronic scanning ultrasonic endoscope 3 supplemented with the header information by the first selector 61 as described above, it is sensed that the echo signal is in a B mode frame by frame in synchronization with a synchronization signal from the electronics-side timing controller 56 by the mode sensing unit 62.

The mode sensing unit 62 detects a B mode according to the header information added line by line by the B mode detecting unit 83 based on the line synchronization signal detected by the line synchronization detecting unit 82, and outputs a B mode detection signal to the B latch unit 85. The mode sensing unit 62 outputs the B mode detection signal from the B latch unit 85 to the second selector 65 and the B mode gate unit 87 frame by frame based on the frame synchronization signal detected by the frame synchronization detecting unit 81. The B mode gate unit 87 outputs an echo signal in a B mode to the B mode arithmetic unit 64 frame by frame based on the B mode detection signal.

Frames of echo signals inputted to the B mode arithmetic unit 64 are each transformed into B mode signals and outputted to the memory controller 66 via the second selector 65.

Frames of B mode signals inputted to the memory controller 66 are each temporarily stored in the frame memory 67 as described above, and then outputted to the video processing unit 38 from the DMA controller 70 via the PCI I/F 71. The video processing unit 38 performs video signal processing such as coordinate transform using the graphic memory 37 according to control by the CPU 39a and displays a monochrome B mode image as an ultrasonic tomographic image on the display screen of the monitor 5.

Figure 7:
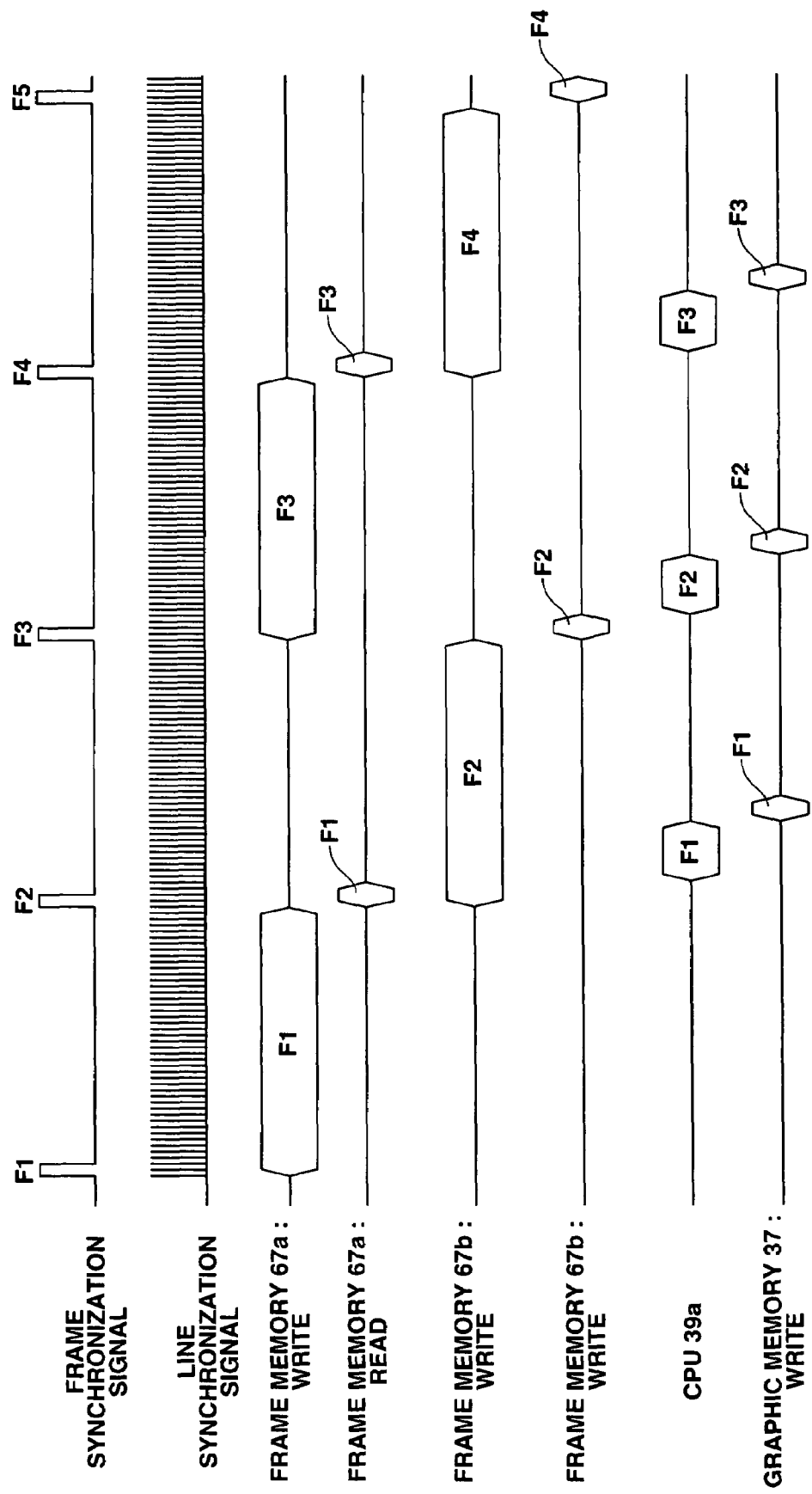

The memory controller 66, the frame memory 67, the arithmetic processor 68 and the arithmetic frame memory 69 operate as shown in FIG. 7, for example.

In FIG. 7, the first column represents frame synchronization signals and the second column represents line synchronization signals. The third column represents write of a B mode signal of first and third frames into the memory 67a in the frame memory 67. The fourth column represents read of the B mode signal of the first and third frames from the memory 67a in the frame memory 67.

The fifth column represents write of a B mode signal of second and fourth frames into the memory 67b in the frame memory 67. The sixth column represents read of the B mode signal of the second and fourth frames from the memory 67b in the frame memory 67. The seventh column represents arithmetic on the B mode signal of the first to third frames by the CPU 39a. The eighth column represents write of the B mode signal of the first to third frames into the graphic memory 37.

The ultrasonic observing apparatus 4 can, as described above, output the B mode signal obtained from the electronic scanning ultrasonic endoscope 3 directly, not via the arithmetic processor 68 to the DMA controller 70, thereby increasing the signal processing speed.

The operator performs ultrasonic diagnosis around the target while viewing a B mode image displayed on the display screen of the monitor 5. The operator uses the mechanical scanning ultrasonic probe 2 for the ultrasonic diagnosis in order to obtain a higher-resolution B mode image.

The operator inserts the mechanical scanning ultrasonic probe 2 through a treatment instrument insertion channel of the electronic scanning ultrasonic endoscope 3 and projects the distal end portion of the insertion portion of the mechanical scanning ultrasonic probe 2 from a channel aperture by a pre-determined distance so as to insert the mechanical scanning ultrasonic probe 2 around the target in a body cavity. In this state, the operator operates the operation setting unit 6 to perform the ultrasonic observation using the mechanical scanning ultrasonic probe 2.

The ultrasonic observing apparatus 4 controls the mechanical scanning ultrasonic probe 2 based on setting indication information inputted to the CPU 39a from the operation setting unit 6. At this time, the CPU 39a receives a connection detecting signal from the connection sensing unit 33, thereby recognizes that the mechanical scanning ultrasonic probe 2 is connected. The CPU 39a controls the machine-side timing controller 44 to output the timing signal to the machine-side ultrasonic driving signal generating unit 41. The machine-side ultrasonic driving signal generating unit 41 generates ultrasonic driving pulses, outputs the ultrasonic driving pulses to the ultrasonic transducer 14, generates a driving signal and outputs the signal to the rotation driving unit 15 based on the timing signal from the machine-side timing controller 44.

As for the mechanical scanning ultrasonic probe 2, the rotation driving unit 15 rotates the flexible shaft 13 and the ultrasonic transducer 14. Depending on the rotation, the ultrasonic transducer 14 repetitively transmits ultrasonic pulses into a living body based on ultrasonic driving pulses and receives an ultrasonic beam reflected in the living body to obtain echo signals successively. The echo signals are received by the machine-side receiving unit 42 and processed into analog signals successively.

The echo signals processed into analog signals are transformed into digital signals by the machine-side A/D converting unit 43 and outputted to the signal processing unit 36. In the signal processing unit 36, the first selector 61 switches the echo signals from the mechanical scanning ultrasonic probe 2 based on scan identification information from the CPU 39a.

The switched echo signals from the mechanical scanning ultrasonic probe 2 are outputted to the B mode arithmetic unit 64 frame by frame. Frames of echo signals inputted to the B mode arithmetic unit 64 are each transformed into B mode signals by the well known arithmetic processing and outputted to the memory controller 66 via the second selector 65.

Frames of B mode signals inputted to the memory controller 66 are each temporarily stored in the frame memory 67, and then outputted from the DMA controller 70 to the video processing unit 38 via the PCI I/F 71.

The video processing unit 38 performs video signal processing such as coordinate transform using the graphic memory 37 according to control by the CPU 39a and displays a monochrome B mode image as an ultrasonic tomographic image on the display screen of the monitor 5. Meanwhile, the memory controller 66, the frame memory 67, the CPU 39a and the graphic memory 37 operate similarly to the B mode scanning by the above described electronic scanning ultrasonic endoscope 3.

The ultrasonic observing apparatus 4 can output the B mode signal obtained from the mechanical scanning ultrasonic probe 2 directly, not via the arithmetic processor 68 to the DMA controller 70, thereby increasing the signal processing speed. The operator views the B mode image obtained from the mechanical scanning ultrasonic probe 2 for more detailed ultrasonic diagnosis.

By the above operations, the ultrasonic diagnostic apparatus 1 according to the present embodiment can acquire an ultrasonic tomographic image entirely around a target using the electronic scanning ultrasonic endoscope 3, and then acquire a detailed ultrasonic tomographic image using the mechanical scanning ultrasonic probe 2.

After the execution of the ultrasonic diagnosis, the operator pulls out the mechanical scanning ultrasonic probe 2 from the treatment instrument insertion channel of the electronic scanning ultrasonic endoscope 3, and inserts a needle (not shown) into the treatment instrument insertion channel for a biopsy. This is to enable execution of definite diagnosis based on the diagnosis in the present embodiment.

The ultrasonic observing apparatus 4 according to the present embodiment can use high frequencies and low frequencies of ultrasonic pulses at the same time with both scanning of electronic scanning and mechanical scanning, so that the apparatus 4 can obtain a deep-invasion and high-resolution ultrasonic tomographic image. Additionally, the ultrasonic observing apparatus 4 according to the present embodiment can output mechanical scanning or electronic scanning B mode signals to the DMA controller 70 directly, not via the arithmetic processor 68, thereby increasing the signal processing speed.

As such, the ultrasonic observing apparatus 4 according to the present embodiment can perform optimal signal processing depending on the arithmetic amount in both scanning of mechanical scanning and electronic scanning by decreasing the arithmetic amount in a B mode and increasing the arithmetic amount in a diagnosis mode such as a color flow mode specific to electronic scanning, thereby improving the frame rate. As a result, the ultrasonic diagnostic apparatus 1 according to the present embodiment can perform both scanning of electronic scanning and mechanical scanning while connecting the mechanical scanning ultrasonic probe 2 and the electronic scanning ultrasonic endoscope 3 to the single ultrasonic observing apparatus 4 and obtain the optimal frame rate depending on scanning.

Figure 8:
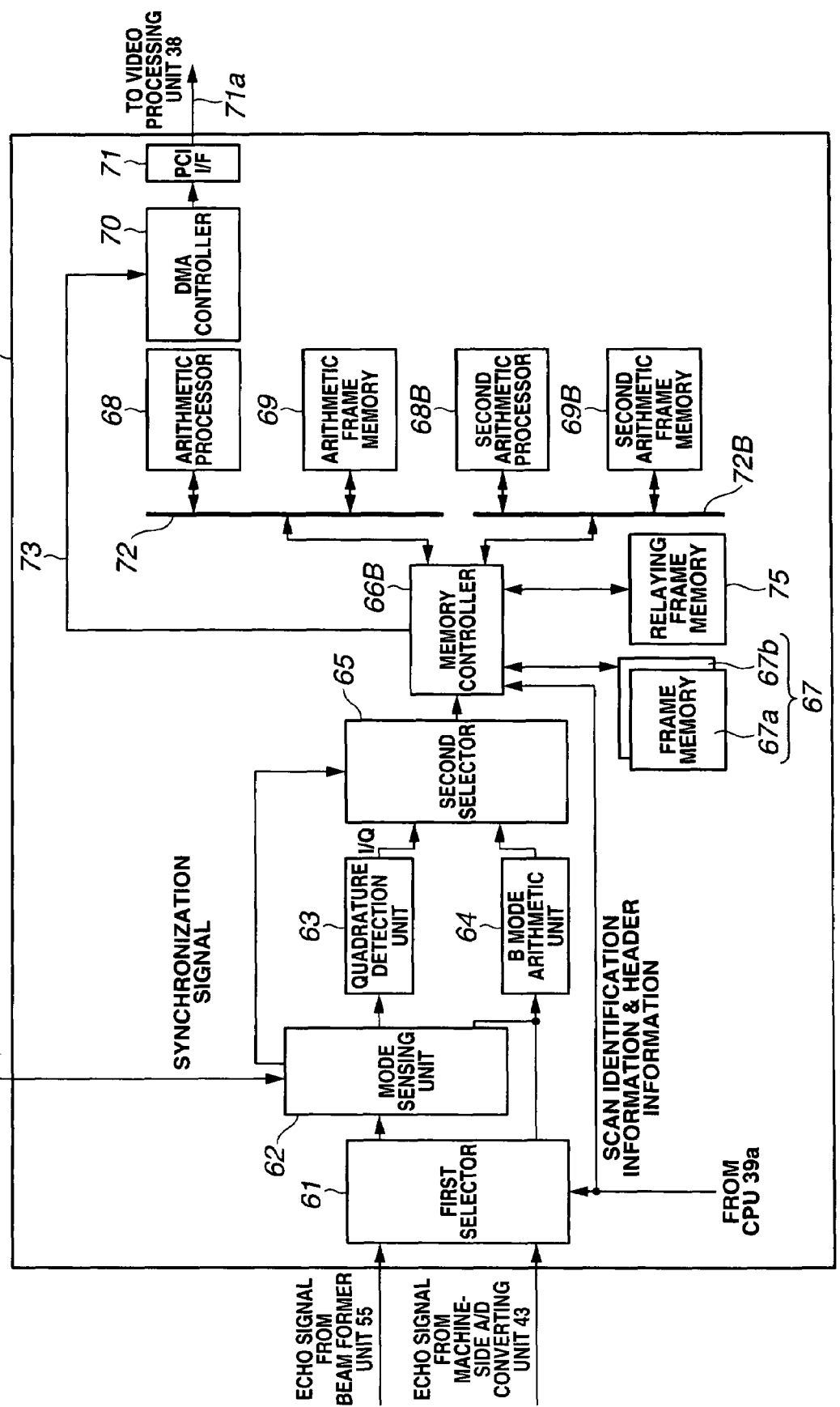
Figure 9:
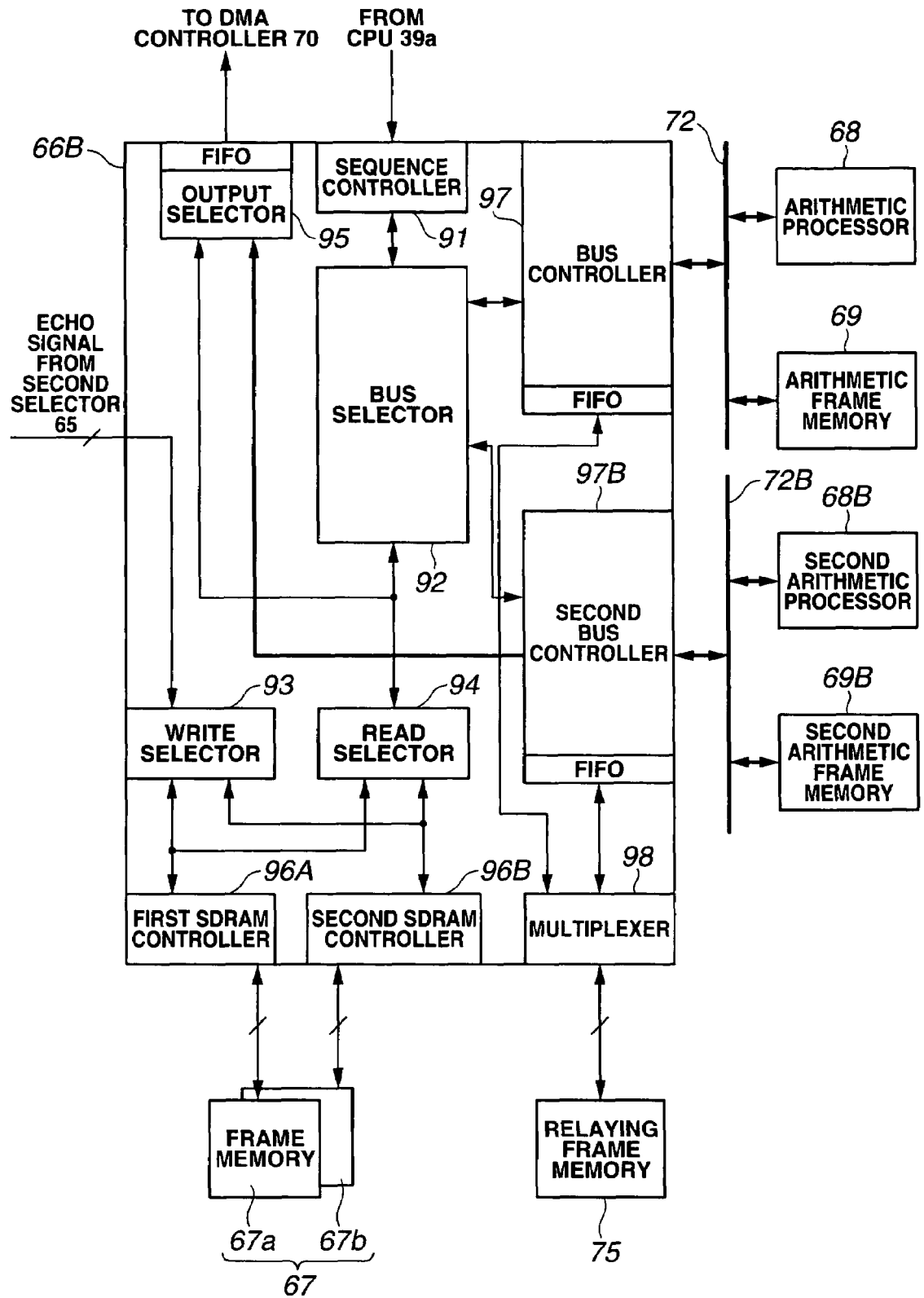

In the above operations, the signal processing unit can further configured of a local bus connecting to an arithmetic processor and the like, for example as shown in FIGS. 8 and 9.

As shown in FIG. 8, a signal processing unit 36B is configured of a relaying frame memory 75 and a memory controller 66B connected to a second arithmetic processor 68B and a second arithmetic frame memory 69B via a second local bus 72B.

The memory controller 66B is configured of a second bus controller 97B connected to the second local bus 72B and a multiplexer 98 connected to the relaying frame memory 75, in addition to the configuration of the memory controller 66.

The memory controller 66B can output a B mode signal obtained from the mechanical scanning ultrasonic probe 2 or the electronic scanning ultrasonic endoscope 3 to the DMA controller 70 directly, not via the arithmetic processor 68 according to control by the sequence controller 91 similarly to the memory controller 66. The memory controller 66B differs from the memory controller 66 in signal flow in a diagnosis mode such as a color flow mode specific to electronic scanning.

In FIG. 9, when, for example, information of a diagnosis mode scan such as an electronic scan in a color flow mode specific to electronic scanning is inputted from the CPU 39a to the sequence controller 91, the write selector 93 writes a B mode signal inputted from the second selector 65 via the first SDRAM controller 96A into the memory 67a in the frame memory 67.

If a frame of data is written into the memory 67a in the frame memory 67, the read selector 94 reads out frame data accumulated in the memory 67a in the frame memory 67 via the first SDRAM controller 96A. The bus selector 92 transfers the frame data read out from the read selector 94 depending on control by the sequence controller 91 into the arithmetic frame memory 69 via the bus controller 97.

When the data transfer of the frame data (a B mode signal) to the arithmetic frame memory 69 is complete, the write selector 93 writes a D mode signal inputted from the second selector 65 via the second SDRAM controller 96B into the memory 67b in the frame memory 67. The arithmetic processor 68 performs arithmetic processing on frame data in the arithmetic frame memory 69 while the ultrasonic endoscope 3 performs a D mode scan. However, since the frame data in the arithmetic frame memory 69 is a B mode signal, the frame data is outputted as it is.

The bus selector 92 reads out the frame data (a B mode signal) in the arithmetic frame memory 69 and transfers the data to the relaying frame memory 75 via the multiplexer 98 through a FIFO memory in the bus controller 97. The bus selector 92 transfers the frame data (a B mode signal) transferred to the relaying frame memory 75 to the second arithmetic frame memory 69B through the FIFO memory in the second bus controller 97B via the multiplexer 98 according to control by the sequence controller 91.

The second arithmetic processor 68B performs arithmetic processing on the frame data in the second arithmetic frame memory 69B, but outputs the frame data in the second arithmetic frame memory 69B as it is since the data is a B mode signal. The bus selector 92 reads out the frame data (a B mode signal) accumulated in the second arithmetic frame memory 69B and outputs the data to the DMA controller 70 via the second bus controller 97B and the FIFO memory in the output selector 95.

On the other hand, if a frame of D mode signal is written into the memory 67b in the frame memory 67, the read selector 94 reads out frame data (a D mode signal) accumulated in the memory 67b in the frame memory 67 via the second SDRAM controller 96B. The bus selector 92 transfers the frame data (a D mode signal) read out from the read selector 94 depending on control by the sequence controller 91 to the second arithmetic frame memory 69B via the second bus controller 97b .

The second arithmetic processor 68B performs arithmetic processing on the D mode signal in the second arithmetic frame memory 69B. After finishing the arithmetic on the second arithmetic processor 68B, the bus selector 92 outputs the frame data accumulated in the second arithmetic frame memory 69B to the DMA controller 70 via the second bus controller 97B and the FIFO memory in the output selector 95.

By repeating the above operations, the signal processing unit 36B can perform signal processing on an echo signal (a D mode signal) from the electronic scanning ultrasonic endoscope 3 using the arithmetic processor 68 or the second arithmetic processor 68B and outputs the result to the DMA controller 70.

For the above processing, the signal processing unit 36B can be configured to use, for example, the arithmetic processor 68 exclusively for a B mode and the arithmetic processor 68B exclusively for a D mode, or configured to process in a B mode and a D mode alternately.

As a result, according to the present variation, effects similar to the first embodiment are obtained as well as both of the arithmetic processor and the arithmetic frame memory are provided, whereby an echo signal from the electronic scanning ultrasonic endoscope 3 can be processed faster in a diagnosis mode such as a color flow specific to electronic scanning.

In the above description of the present embodiment, an ultrasonic endoscope for the electronic scanning and an ultrasonic probe for mechanical scanning are used and the mechanical scanning ultrasonic probe 2 and the electronic scanning ultrasonic endoscope 3 are detachably connected to the ultrasonic observing apparatus 4. However, the present invention is not limited to the configuration, and an ultrasonic probe for the electronic scanning and an ultrasonic endoscope for mechanical scanning can be used and a mechanical scanning ultrasonic endoscope and an electronic scanning ultrasonic probe can be detachably connected to the ultrasonic observing apparatus.

In the present invention it is apparent that aspects differing in a wide scope can be made based on the present invention without deviating from the sprit and scope of the invention. The present invention is not constrained by the particular aspects thereof, but is limited only by the appended claims.

What is claimed is:

1. An ultrasonic observing apparatus comprising:
a scanning identifying unit for
identifying an echo signal obtained by a first ultrasonic sending/receiving unit for transmitting ultrasonic pulses toward a target and receiving ultrasonic pulses reflected from the target by mechanical scanning,
identifying an echo signal obtained by a second ultrasonic sending/receiving unit for transmitting ultrasonic pulses toward the target and receiving ultrasonic pulses reflected from the target by electronic scanning, and
adding predetermined identification information to the echo signal from the second ultrasonic sending/receiving unit based on setting indication information of an observation mode of B mode or D mode;
a B mode arithmetic unit for generating a B mode signal of the B mode from an echo signal obtained from the first ultrasonic sending/receiving unit and the second ultrasonic sending/receiving unit;
an arithmetic processor for performing arithmetic processing for the D mode; and
a signal processing unit for performing signal processing on the echo signal obtained by the first ultrasonic sending/receiving unit and on the echo signal obtained by the second ultrasonic sending/receiving unit, wherein:
the signal processing unit determines whether the observation mode is the B mode or D mode based on the setting indication information and on the predetermined identification information which the scanning identifying unit added to the echo signal from the second ultrasonic sending/receiving unit, and
when the echo signal from the first ultrasonic sending/receiving unit and the second ultrasonic sending/receiving unit is an echo signal in the B mode, generates a B mode signal in the B mode by the B mode arithmetic unit,
when the echo signal from the second ultrasonic sending/receiving unit is an echo signal in the D mode, performs arithmetic processing on the echo signal from the second ultrasonic sending/receiving unit using the arithmetic processor, and
when the echo signal from the second ultrasonic sending/receiving unit is an echo signal in the B mode, passes the B mode signal generated by the B mode arithmetic unit through the arithmetic processor without performing arithmetic processing on the B mode signal in the arithmetic processor.

2. A control method for an ultrasonic observing apparatus comprising:
a scanning identifying step of identifying an echo signal obtained by a first ultrasonic sending/receiving unit for transmitting ultrasonic pulses toward a target and receiving ultrasonic pulses reflected from the target by mechanical scanning, identifying an echo signal obtained by a second ultrasonic sending/receiving unit for transmitting ultrasonic pulses toward the target and receiving ultrasonic pulses reflected from the target by electronic scanning, and adding predetermined identification information to the echo signal of the ultrasonic wave from the second ultrasonic sending/receiving unit based on setting indication information of an observation mode of B mode or D mode; and
a step of determining whether the observation mode is the B mode or the D mode based on the setting indication information and on the predetermined identification information which the scanning identifying step added to the echo signal from the second ultrasonic sending/receiving unit, a step of generating a B mode signal in the B mode by the B mode arithmetic unit when the echo signal from the first ultrasonic sending/receiving unit and the second ultrasonic sending/receiving unit is an echo signal in the B mode;

a signal processing step of performing arithmetic processing using an arithmetic processor that performs arithmetic processing for the D mode when the echo signal from the second ultrasonic sending/receiving unit is an echo signal in the D mode, and passing the B mode signal generated by the B mode arithmetic unit with respect to the echo signal from the second ultrasonic sending/receiving unit through the arithmetic processor without performing arithmetic processing on the B mode signal in the arithmetic processor when the echo signal from the second ultrasonic sending/receiving unit is an echo signal in the B mode.

3. An ultrasonic diagnostic apparatus comprising:

an ultrasonic observing apparatus for creating an ultrasonic tomographic image, the apparatus connecting to a mechanical scanning ultrasonic probe or mechanical scanning ultrasonic endoscope, and an electronic scanning ultrasonic probe or electronic scanning ultrasonic endoscope;

a mechanical transducer echo signal detecting unit, provided in the ultrasonic observing apparatus, for transmitting ultrasonic pulses from an ultrasonic transducer built in the mechanical scanning ultrasonic probe or mechanical scanning ultrasonic endoscope to living body tissue and detecting an echo signal obtained by receiving ultrasonic pulses reflected from the living body tissue;

an electronic transducer echo signal detecting unit, provided in the ultrasonic observing apparatus, for transmitting ultrasonic pulses from an ultrasonic transducer built in the electronic scanning ultrasonic probe or electronic scanning ultrasonic endoscope to living body tissue and detecting an echo signal obtained by receiving ultrasonic pulses reflected from the living body tissue;

a video processing unit, provided in the ultrasonic observing apparatus, for generating the ultrasonic tomographic image;

a central processing unit, provided in the ultrasonic observing apparatus, for controlling the video processing unit; and a signal processing unit, provided in the ultrasonic observing apparatus, for performing signal processing on the echo signal from the mechanical transducer echo signal detecting unit and the echo signal from the electronic transducer echo signal detecting unit, the signal processing unit including:

a scanning identifying unit for adding predetermined identification information to an echo signal from the electronic transducer echo signal detecting unit based on setting indication information for indicating an observation mode in B mode or D mode, an arithmetic processor for performing arithmetic processing for the D mode on the echo signal obtained by the ultrasonic transducer of the electronic scanning ultrasonic probe or electronic scanning ultrasonic endoscope, and a B mode arithmetic unit for performing signal processing for the B mode on an echo signal obtained by the ultrasonic transducer of the ultrasonic probe or ultrasonic endoscope by the mechanical scanning and the ultrasonic probe or ultrasonic endoscope by the electronic scanning, wherein, the signal processing unit determines whether the observation mode is the B mode or the D mode based on the setting indication information and on the predetermined identification information which the scanning identifying unit added to the echo signal from the second ultrasonic sending/receiving unit, and when the observation mode is the B mode, the signal processing unit performs signal processing on the echo signal obtained from the ultrasonic transducer of the mechanical scanning ultrasonic probe or the mechanical scanning ultrasonic endoscope and the electronic scanning ultrasonic probe or the electronic scanning ultrasonic endoscope in the B mode arithmetic unit so as to generate a B mode signal, and passes the B mode signal in the B mode generated by the B mode arithmetic unit through the arithmetic processer without performing arithmetic processing on the B mode signal in the arithmetic processor and transfers the B mode signal to the video processing unit, and when the observation mode is the D mode, the signal processing unit performs by the arithmetic processor arithmetic processing on the echo signal obtained from the ultrasonic transducer of the electronic scanning ultrasonic probe or the electronic scanning ultrasonic endoscope.

4. The ultrasonic observing apparatus according to claim 1, further comprising a DMA controller, wherein the echo signal in the B mode obtained by the first ultrasonic sending/receiving unit is outputted by the DMA controller, and the echo signal in the B mode obtained by the second ultrasonic sending/receiving unit is passed through the arithmetic processor and then outputted by the DMA controller.

5. The control method for an ultrasonic observing apparatus according to claim 2, further comprising:

a first output step of outputting by a DMA controller the echo signal in the B mode obtained by the first ultrasonic sending/receiving unit; and a second output step of passing the echo signal in the B mode obtained by the second ultrasonic sending/receiving unit through the arithmetic processor and then outputting the echo signal by the DMA controller.

6. The ultrasonic diagnostic apparatus according to claim 3, wherein the signal processing unit uncludes a DMA controller, the echo signal in the B mode obtained by the first ultrasonic sending/receiving unit is outputted by the DMA controller, and the echo signal in the B mode obtained by the second ultrasonic sending/receiving unit is passed through the arithmetic processor and then outputted by the DMA controller.

* * * * *